United States Patent
Shoenfeld

[11] Patent Number: 5,816,797
[45] Date of Patent: Oct. 6, 1998

[54] DRY WARMING METHOD AND DEVICE FOR PREPARING THERMOPLASTIC MATERIALS

[75] Inventor: Harold Shoenfeld, Brooklyn, N.Y.

[73] Assignee: S&S X-Ray Products, Inc., Brooklyn, N.Y.

[21] Appl. No.: 684,449

[22] Filed: Jul. 19, 1996

[51] Int. Cl.⁶ ...................................................... F27D 11/00
[52] U.S. Cl. .............................................. 432/33; 219/385
[58] Field of Search ............................. 432/33; 219/385, 219/386

[56] References Cited

U.S. PATENT DOCUMENTS

| | | | |
|---|---|---|---|
| 2,031,995 | 2/1936 | Yost | 219/386 X |
| 3,126,882 | 3/1964 | Hilfiker | 219/386 X |
| 3,644,708 | 2/1972 | Edwards | 219/386 |
| 4,256,952 | 3/1981 | Thomas et al. | 219/386 X |
| 4,303,828 | 12/1981 | Thomas et al. | 219/386 X |
| 4,369,355 | 1/1983 | Helixon | 219/386 X |
| 4,910,386 | 3/1990 | Johnson | 219/385 |
| 5,140,136 | 8/1992 | Fellows et al. | 219/386 X |
| 5,408,576 | 4/1995 | Bishop | 219/386 X |
| 5,496,987 | 3/1996 | Siccardi et al. | 219/386 |

*Primary Examiner*—Christopher Kilner
*Attorney, Agent, or Firm*—Bromberg & Sunstein LLP

[57] ABSTRACT

A method for preparing a thermoplastic material, with dry heat, for use in patient fixation. The method includes generating heat to a threshold temperature and transferring the heat to the thermoplastic material by a heat conductive path. Once the thermoplastic material has become pliable, it is molded into a cast for fixation purposes. The heat may be generated by a device having a housing and a member movable attached to the housing. The device also includes a heating element for providing a heat conductive path to the member.

20 Claims, 3 Drawing Sheets

DRY WARMING METHOD AND DEVICE FOR PREPARING THERMOPLASTIC MATERIALS

TECHNICAL FIELD

The present invention generally relates to a method for preparing thermoplastic materials, and in particular, to a method for preparing thermoplastic materials, using dry heat, to be used in patient fixation. A device is also set forth for warming the sheets of a thermoplastic material.

BACKGROUND ART

When carrying out certain medical procedures, for example, radiation therapy or orthopedic settings, thermoplastic materials are frequently used on a patient for fixation (i.e., casting) purposes. In general, thermoplastic materials, when warmed to a temperature within a threshold range, become easily pliable, and, when cooled below that threshold range, become relatively rigid. To this end, thermoplastic materials are often warmed and molded into a shape which complements a body part on a patient, so as to help the patient maintain that particular body part in a required fixed position for an extended period of time. For example, in radiation therapy involving the head area, a patient may find it difficult to maintain his head in a certain position for the entire treatment. As such, a thermoplastic material may be warmed and molded into a cast corresponding to the shape of the patient's head for maintaining the patient's head in the required position. The thermoplastic material may also be used for orthopedic purposes. For example, by setting a cast of thermoplastic material about an arm or leg having a bone fracture, movement of the arm or leg may be minimized to aid in the healing of the fracture.

Currently, to transform the thermoplastic material from a relatively rigid to a more pliable state, the thermoplastic material is soaked in a hot water bath. However, the use of a water bath is not always preferable. In particular, a water bath is generally bulky and large in size. As such, the water bath may take up much of the needed space in a limited work area. Moreover, as water tends to evaporate quickly when it is heated, the water bath may need to be refilled regularly. A warm pool of water in the water bath can also promote bacterial growth. As a result, the water bath may need to be drained and cleaned more often than desirable. In addition, when the thermoplastic material is removed from the water bath, or when the water bath is being refilled or cleaned, there is always a risk of dripping or spilling contaminated water onto an otherwise clean work area. The contaminated water may also subsequently be spread to cross-contaminate other clean work areas and/or sterile instruments in those areas.

Accordingly, it is desirable that a cast for fixation purposes may be formed from a thermoplastic material that has been warmed to a pliable state by a safe, dry, and clean method and device.

SUMMARY OF THE INVENTION

In accordance with one embodiment of the present invention, a method is provided for preparing a thermoplastic material, for instance, polycaprolactone, with dry heat, so that the thermoplastic material may be used for fixation purposes. The dry heat, when applied to the sheet of thermoplastic material, transforms the thermoplastic material from a relatively rigid state to a more pliable state. Once the thermoplastic material has been warmed to a more pliable state, the material may subsequently be molded into a cast, for example, for immobilization purposes. To warm the thermoplastic material so that the method of the present invention may be achieved, a device is provided which includes a housing and a member movably mounted to the housing for alternately moving between a closed position and an open position with respect to the housing. A support surface is disposed on the member for accommodating the thermoplastic material thereon. The device also includes a heating element for providing a dry, heat conductive path to the support surface of the member. The heating element is capable of generating heat within a threshold range necessary for transforming the thermoplastic material into a more pliable state. In one embodiment of the invention, the support surface of the member includes a heat conductive panel upon which the thermoplastic material may be placed. To preserve the dry, heat conductive path between the heating element and the conductive panel, the device of the present invention is designed so that the conductive panel is disposed directly against the heating element when heat is generated from the heating element. In a preferred embodiment of the invention, the heating element is provided with a shape substantially similar to the shape of the conductive panel, so that heat from the heating element may be distributed uniformly across the conductive panel. The device may also include a temperature regulator to maintain the heating element at a set threshold temperature, which is preferably between about 140° F. and 180° F. The use of a temperature regulator avoids the need to constantly check on the status of the thermoplastic material by ensuring that once the thermoplastic material has been transformed to the more pliable state, the heating element does not generate heat beyond the required temperature, which may decharacterize the thermoplastic material, or cool down below the required temperature, which may return the thermoplastic material to its rigid form. As such, the thermoplastic material may remain within the device for an extended period, or until the thermoplastic material is used. It is also desirable to prevent the thermoplastic material from sticking to the conductive panel. To prevent such sticking, the conductive panel may include a non-stick layer, for instance, Teflon®.

DETAILED DESCRIPTION OF SPECIFIC EMBODIMENTS

Figure 1:
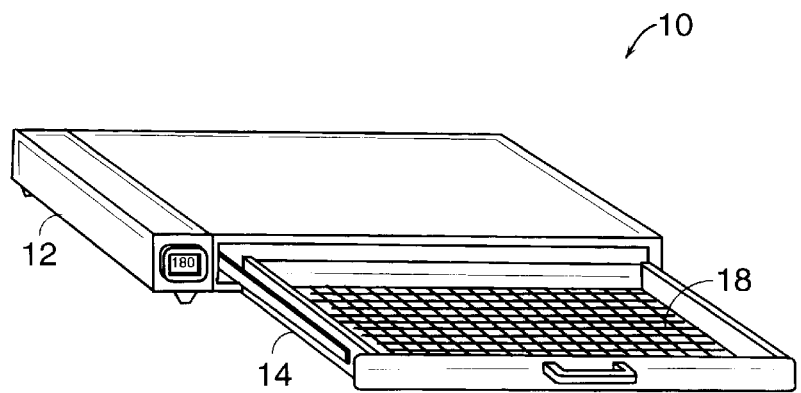
FIG. 1 is a perspective view of a device, for performing the method of the present invention, in an open position.
Figure 2:
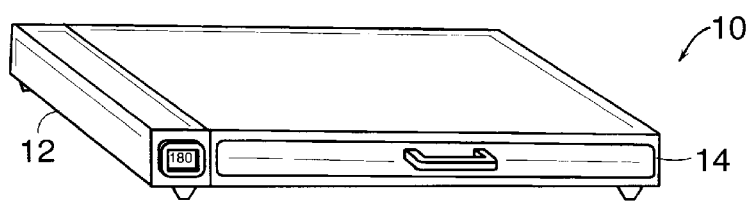
FIG. 2 is a perspective view of the device of FIG. 1 the member in a closed position.

Referring now to the drawings, FIGS. 1 and 2 illustrate a device 10 for dry warming a thermoplastic material from which a cast may be formed in accordance with a method of the present invention. The device 10 includes a housing 12, and a member 14 movably mounted to the housing 12 at mounting mechanism 16 (see FIG. 4). The member 14 is mounted such that it is capable of being alternately moved between an open position, as shown in FIG. 1, and a closed position, as shown in FIG. 2, with respect to the housing 12. A support surface 18 is disposed on the member 14 for supporting a thermoplastic material. The member 14, in a preferred embodiment of the invention, is designed to hold a sheet of thermoplastic material measuring up to approximately 18 inches long, 24 inches wide, and about 0.25 inch thick. The housing 12, on the other hand, is designed with measurements only slightly larger than that of member 14. In this manner, the device 10 may be stored neatly without taking up needed space in a work area. In a one embodiment of the invention, the housing 12 measures approximately 31.125 inches wide, 23 inches deep, and 4.437 inches high. As the housing 12 and member 14 must withstand temperatures within a range sufficient to transform the thermoplastic material from a relatively rigid state to a more pliable state, the housing 12 and member 14 are preferably made from a strong metallic material such as stainless steel. Of course, the housing 12 and the member 14 may be made from other metallic or non-metallic materials.

Figure 3:
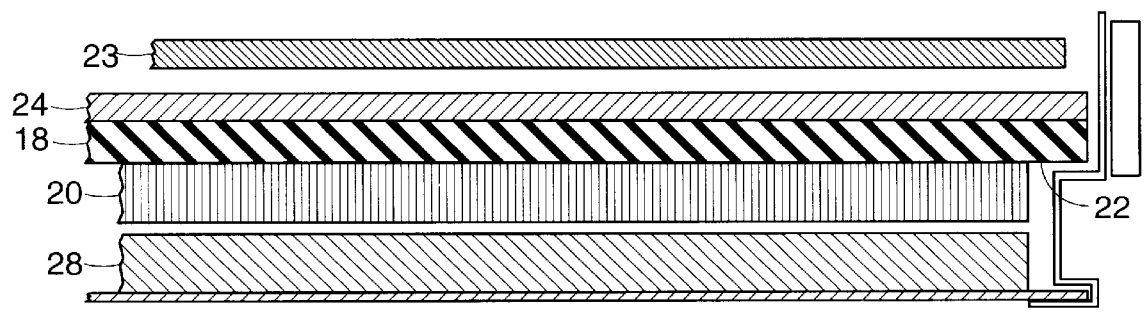
FIG. 3 is partial cross-sectional view of the member shown in FIGS. 1 and 2.
Figure 4:
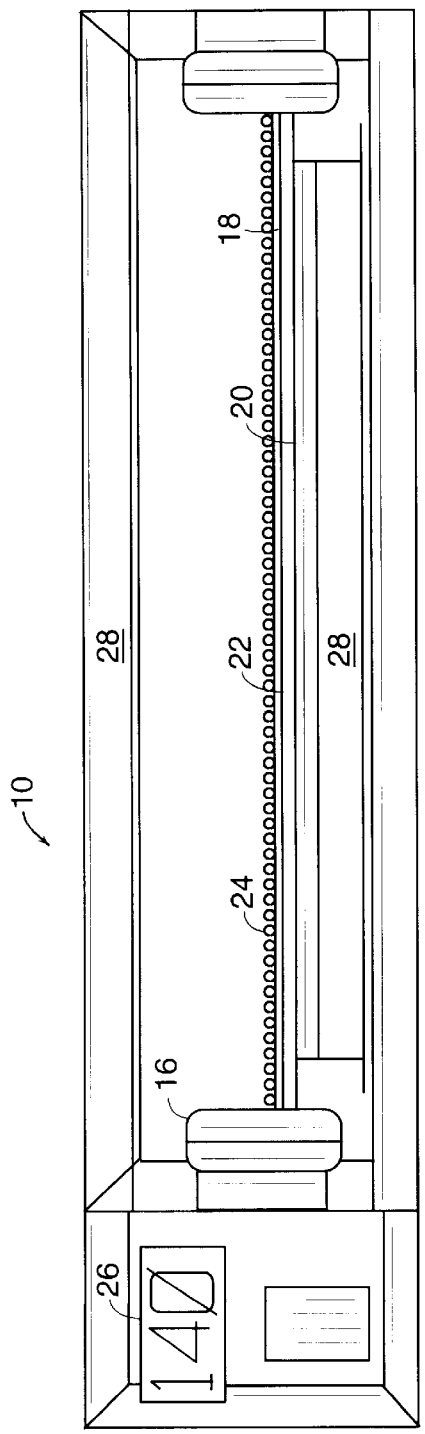
FIG. 4 is a front end view of the device shown in FIG. 1.

Looking now at FIGS. 3 and 4, the device 10 further includes a heating element 20 for providing a dry, heat conductive path to the support surface 18. The heating element 20 can preferably generate heat to within a threshold range of from about 140° F. to about 180° F., necessary for transforming the thermoplastic material from a relatively rigid state to a more pliable state. In the preferred embodiment of the invention, the heating element 20 is a silicone-based heating element, similar to a flexible 120V Benchmark Thermal heater model BF 4009, manufactured by Benchmark Thermal of Grass Valley, Calif. The heating element 20 is preferably sized with a shape similar in dimensions to that of member 14, so that the heat generated by the heating element 20 may be uniformly distributed across the support surface 18. Moreover, depending on the dimensions and composition of the thermoplastic material, the heating element 20 is capable of heating the thermoplastic material and transforming it to a pliable state in about five to about fifteen minutes. Although a silicone-based heating element is presently preferred, it should be appreciated that other heating elements, such as a conventional copper-wire mesh heating element, may be used so long as heat is generated substantially uniformly across the support surface 18. To provide the necessary dry, heat conductive path to the support surface 18, the heating element 20, in one embodiment of the invention, is disposed within the member 14 so that it sits directly against and beneath the support surface 18. Alternatively, the heating element 20 may be disposed within the housing 12, such that when the member 14 is moved into a closed position relative to the housing 12, the heating element 20 is situated directly against and beneath the support surface 18 to maintain a heat conductive path.

With reference now to FIG. 3, the support surface 18, in accordance with one embodiment of the invention, may be in the form of a heat conductive panel 22 or a grill. The conductive panel 22, extending substantially along the entire length of the member 14, is preferably made from a material which can transfer heat from the heating element 20 to a sheet 23 of thermoplastic material in a dry environment by way of conduction. The material from which the conductive panel 22 is made must also allow the panel to maintain its structural integrity when it is heated to a temperature range which corresponds to the temperature range necessary for transforming the sheet 23 of thermoplastic material into a more pliable state. A material such as aluminum, copper, or stainless steel is presently preferred.

Figure 5:
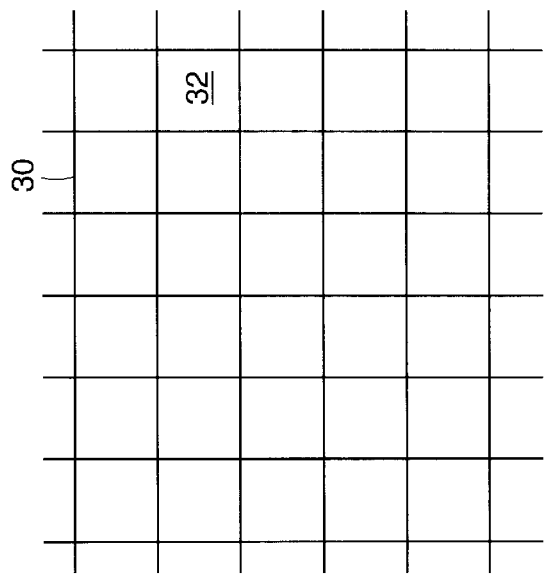
FIG. 5 illustrates a non-stick coating for use in the device of FIG. 1.

The conductive panel 22 may include a non-stick layer 24, similar to that shown in FIG. 5. This is because in some instances, the thermoplastic material, when warmed to a temperature sufficient to make it pliable, may stick to the conductive panel 22. Thus, by having a non-stick layer 24 on the conductive panel 22, the release characteristic between the thermoplastic material and the conductive panel 22 may improve. A non-stick layer 24 similar to the McMaster-Carr Teflon®-coated fiberglass cloth, series number 87885K, which can withstand an application temperature of up to 500° F., is currently preferred. (The McMaster-Carr Teflon®-coated cloth may be obtained from McMaster-Carr located in Dayton, N.J.) A Conwed® Vexar® Diamond Net, or the Conwed® Square Net, having as a primary resin, polypropylene, high density polyethylene, low density polyethylene, low low density polyethylene, ethylvinyl acetate, or radiation-resistant polypropylene, and being capable of withstanding a maximum application temperature of 200° F., may also be used. (The Conwed® Diamond and Square Nets may be obtained from Internet, Inc. located in Minneapolis, Minn.). In one embodiment of the invention, the non-stick layer 24 preferably has a thickness ranging from approximately 0.014 inch to approximately 0.110 inch, and is provided about the entire periphery of the conductive panel 22. However, it should be appreciated that a non-stick layer 24 provided only on the one side of the panel 22 in contact with the sheet 23 of thermoplastic material is sufficient.

The device 10 further includes a temperature regulator 26, as shown in FIG. 4. The temperature regulator 26 is provided to maintain the heating element 20 at a set threshold temperature sufficient to allow the thermoplastic material to remain in a pliable state. In the presently preferred embodiment of the invention, the set threshold temperature is within a range of from about 140° F. to about 180° F., depending on the thermoplastic material being used. For example, if the thermoplastic material is polycaprolactone, a set temperature of about 160° F.±5° F. is needed. The temperature regulator 26 may also help to eliminate the need to constantly check the status of the thermoplastic material while it is in the device 10. In particular, the regulator 26 ensures that once the heating element 20 has reached the set threshold temperature, the heating element 20 does not generate heat beyond, or cool down below the required temperature. In this manner, the thermoplastic material may remain indefinitely within the device 10, or until the thermoplastic material is used. The presently preferred temperature regulator 26 is a Watlow Series 935 regulator having a single temperature sensor input from a thermocouple, and a dual control output. The input is generally positioned adjacent to the regulator 26. (The Watlow Series 935 regulator is manufactured by Watlow Controls in Winona, Minn.).

The device 10, still looking at FIG. 4, may also include an insulating material 28 along the interior of the housing 12. The insulation material 28 preferably allows the housing 12 to retain heat therein so as to reduce the amount of time needed to transform the thermoplastic material into a pliable state. The insulation material 28 also helps to prevent the outer surface of the housing 12 from becoming dangerously hot. In one embodiment of the invention, the insulating material 28 is made from lightweight polyamide foam having a thickness of approximately 0.5 inch. The polyamide foam is preferred because it is inherently fire resistant, having no significant off gassing, and is capable of withstanding an application temperature of up to 370° F. The polyamide foam for use as insulation material 28 in the present invention is similar to the Claremont Low-K 200 insulator which can be obtained from Claremont Sales Corp. of Meriden, Conn.

Figure 6A:
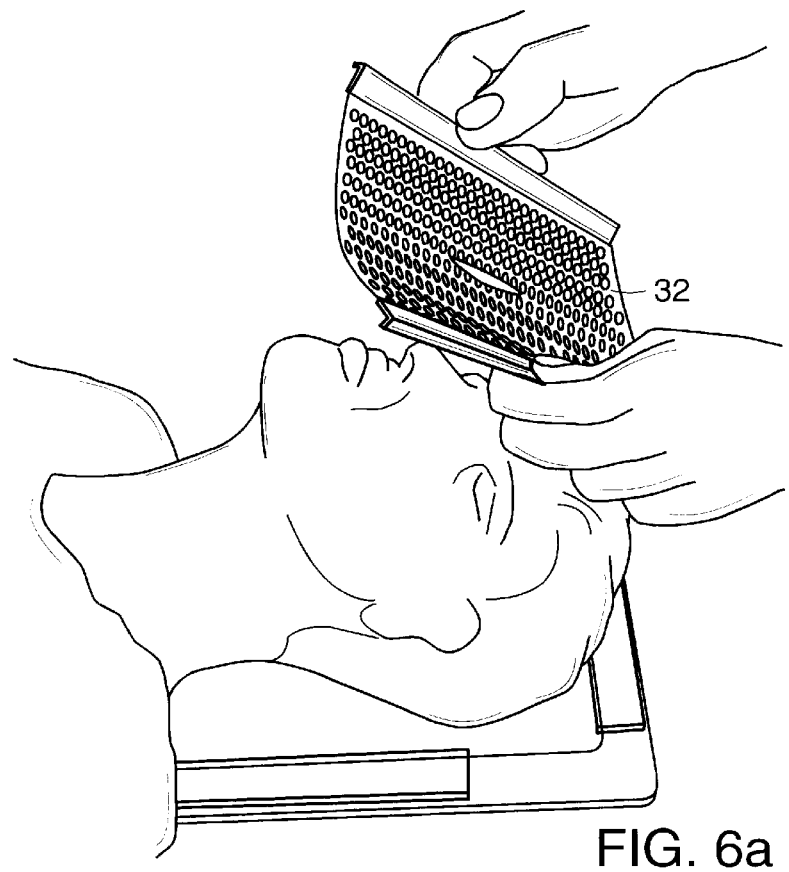
FIGS. 6A–B illustrate a thermoplastic material being used for fixation purposes.
Figure 6B:
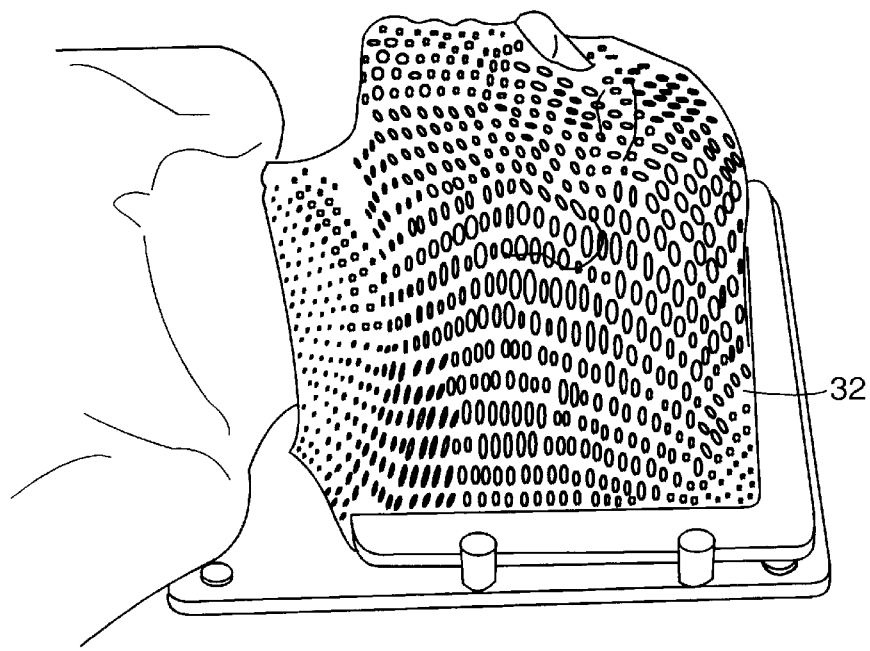

The device 10 provides means for warming a sheet of thermoplastic material in a dry environment, such that the material may be prepared in accordance with a method of the present invention. In particular, as the heat applied to the sheet 23 of thermoplastic material is through a dry conductive panel 22, rather than a wet water bath, the sheet 23 may be transformed from a relatively rigid state to a more pliable state, in a safe, dry and clean environment, such that the chances of accidentally contaminating an otherwise clean work area are minimized. The sheet 23 of thermoplastic material, while pliable, may subsequently be molded into a cast 32, as shown in FIGS. 6a–6b, having a shape for complementarily receiving a part of a patient which requires immobilization. To warm the sheet 23 of thermoplastic material, such as polycaprolactone, the sheet 23 may be placed on the conductive panel 22, preferably having a non-stick surface 24, in the member 14 of the device 10. The member 14, with the thermoplastic material 23 thereon, may thereafter be moved to within the housing 12. Next, the temperature regulator 26 may be set to a threshold temperature sufficient to transform the sheet 23 of thermoplastic material from a relatively rigid state to a more pliable state. A temperature of about 160° F. is required when the thermoplastic material used is polycaprolactone. Alternatively, the device 10 of the present invention may be preheated to the desired temperature prior to placing the sheet 23 of thermoplastic material within the housing 12. It should be appreciated that heat transference from the heating element 20 to the thermoplastic material is substantially by conduction. However, because the non-stick layer 24 may have a net-like design, as illustrated in FIG. 5, the sheet 23 of thermoplastic material may sit only on filaments 30 comprising the net. To this end, heat transference to the sheet 23 of thermoplastic material may, in a small amount, be by convection through the openings 32 in the net. A small amount of heat generated by the heating element 20 may also radiate up the side of the housing 12 before being reflected down, by the insulation material 28, to the top side of sheet 23 not in direct contact with the conductive panel 22. Once the sheet 23 of thermoplastic material has reached the desirable pliable state, the sheet 23 may be pulled from within the housing 12, and removed from the conductive panel 22. The sheet of thermoplastic material, while still pliable, may be molded into a cast having an appropriate shape for immobilizing a particular body part on the patient. The sheet thermoplastic material can subsequently be cast about that particular body part and allowed to harden.

Although the device 10 of the present invention, as shown in FIGS. 1 and 2, employs a member 14 which may be moved in a sliding motion completely within the housing 12, it is contemplated that a device having a member hingedly mounted to the housing may also be employed. While the invention has been described in connection with specific embodiments thereof, it will be understood that it is capable of further modification. This application is intended to cover any variations, uses, or adaptations of the invention and including such departures from the present disclosure as come within known or customary practice in the art to which the invention pertains.

What is claimed is:

1. A device for warming a thermoplastic material so that the material may be prepared for use on a patient, the device comprising:
   a housing;
   a member movably mounted to the housing and being alternately movable between a closed position and an open position with respect to the housing;
   a support surface disposed on the member for supporting the thermoplastic material; and
   a heating element for distributing heat substantially uniformly over a planar surface area coincident with the element, the planar surface area of the heating element being in contact with the member.

2. A device according to claim 1 wherein the heating element is disposed in the member so that the heating element is in direct contact with the support surface.

3. A device for warming a thermoplastic material so that the material may be prepared for use on a patient, the device comprising:
   a housing;
   a member movably mounted to the housing and being alternately movable between a closed position and an open position with respect to the housing;
   a support surface disposed on the member for supporting the thermoplastic material; and
   heating element for distributing heat substantially uniformly over a planar surface area coincident with the element, the heating element being disposed in the housing such that when the member is moved to a closed position, the heating element is in direct contact with the support surface.

4. A device according to claim 1 wherein the support surface includes a non-stick layer.

5. A device according to claim 1 further comprising a temperature regulator for maintaining the heating element at a set temperature.

6. A device according to claim 1 wherein the housing includes an insulation material to maintain heat within the housing.

7. A device according to claim 1 wherein the member is slidable with respect to the housing.

8. A device for warming a thermoplastic material into a pliable form for use in patient fixation, the device comprising:
   a housing;
   a member movably mounted to the housing;
   a conductive panel positioned on the member and having a surface for supporting the thermoplastic material thereon above the member; and
   a heating element disposed in the member beneath the surface of the conductive panel to provide a heat conductive path to the surface of the conductive panel.

9. A device according to claim 8 wherein the heating element distributes heat substantially uniformly across the support surface of the conductive panel.

10. A device according to claim 8 wherein the conductive panel includes a non-stick layer on the support surface.

11. A device according to claim 8 further comprising a temperature regulator for maintaining the heating element at a set temperature.

12. A device according to claim 8 wherein the housing includes an insulation material to maintain heat within the housing.

13. A device for warming a thermoplastic material into a pliable form for use in patient fixation, the device comprising:
   a housing;
   a member movably mounted to the housing and capable of moving between a closed position and an open position relative to the housing;
   a conductive panel situated on the member and having a surface for supporting the thermoplastic material thereon; and a heating element disposed within the housing for providing heat substantially uniformly over a planar surface area coincident with the element, such that when the member is moved into the closed position, the heating element is in approximation with the conductive panel beneath the surface of the panel so as to provide a heat conductive path to the surface of the panel.

14. A device according to claim 13 wherein the heating element distributes heat substantially uniformly across the support surface of the conductive panel.

15. A device according to claim 13 wherein the conductive panel includes a non-stick layer on the support surface.

16. A device according to claim 13 further comprising a temperature regulator for maintaining the heating element at a set temperature.

17. A device according to claim 13 wherein the housing includes an insulation material to maintain heat within the housing.

18. A device according to claim 1, wherein the heating element is sized with a shape similar in dimensions to that of the member, so that heat generated by the heating element may be uniformly distributed across the support surface.

19. A device according to claim 8, wherein the heating element is sized with a shape similar in dimensions to that of the member, so that heat generated by the heating element may be uniformly distributed across the conductive panel.

20. A device according to claim 13, wherein the heating element is sized with a shape similar in dimensions to that of the member, so that heat generated by the heating element may be uniformly distributed across the conductive panel.

* * * * *